(12) United States Patent
Varshavskaya et al.

(10) Patent No.: US 11,054,346 B2
(45) Date of Patent: Jul. 6, 2021

(54) DETECTING A SUBSTRATE (71) Applicant: RareCyte, Inc., Seattle, WA (US)

(72) Inventors: Paulina Varshavskaya, Seattle, WA (US); Edward Shafer, Bellevue, WA (US); Steve Quarre, Woodinville, WA (US); Ronald Seubert, Sammamish, WA (US)

(73) Assignee: RareCyte, Inc., Seattle, WA (US)

( * ) Notice: Subject to any disclaimer, the term of this patent is extended or adjusted under 35 U.S.C. 154(b) by 465 days.

(21) Appl. No.: 15/922,736

(22) Filed: Mar. 15, 2018

(65) Prior Publication Data
US 2018/0202901 A1      Jul. 19, 2018

Related U.S. Application Data

(63) Continuation-in-part of application No. 14/989,907, filed on Jan. 7, 2016, now Pat. No. 10,072,927, and a continuation-in-part of application No. 15/484,925, filed on Apr. 11, 2017, now Pat. No. 10,088,392, which is a continuation-in-part of application No. 15/275,416, filed on Sep. 25, 2016, now Pat. No. 9,810,605, which is a continuation of application No. 14/248,510, filed on Apr. 9, 2014, now Pat. No. 9,519,002.

(60) Provisional application No. 62/326,502, filed on Apr. 22, 2016, provisional application No. 61/810,834, filed on Apr. 11, 2013, provisional application No. 61/922,931, filed on Jan. 2, 2014.

(51) Int. Cl.
| | | |
|---|---|---|
| G01N 15/10 | (2006.01) | |
| G01N 35/10 | (2006.01) | |
| C12M 1/26 | (2006.01) | |
| G01M 1/14 | (2006.01) | |
| G01N 1/14 | (2006.01) | |
| G01N 35/00 | (2006.01) | |
| B01L 3/02 | (2006.01) | |

(52) U.S. Cl.
CPC ............. *G01N 1/14* (2013.01); *B01L 3/0217* (2013.01); *C12M 33/04* (2013.01); *G01N 35/0098* (2013.01); *G01N 35/109* (2013.01); *G01N 35/1009* (2013.01); *G01N 35/1011* (2013.01); *B01L 2200/0657* (2013.01); *B01L 2200/0668* (2013.01); *B01L 2300/14* (2013.01); *B01L 2400/0478* (2013.01); *B01L 2400/0487* (2013.01); *G01N 2001/1454* (2013.01); *G01N 2015/1006* (2013.01); *G01N 2015/1081* (2013.01)

(58) Field of Classification Search
None
See application file for complete search history.

(56) References Cited

U.S. PATENT DOCUMENTS

| 4,613,573 A | * | 9/1986 | Shibayama | ............ C12M 33/02 356/244 |
|---|---|---|---|---|
| 5,106,584 A | * | 4/1992 | Funakubo | ............ G01N 35/028 422/63 |
| 5,705,814 A | * | 1/1998 | Young | .................... G01Q 30/06 250/307 |

(Continued)

*Primary Examiner* — Benjamin R Whatley
*Assistant Examiner* — Brittany I Fisher
(74) *Attorney, Agent, or Firm* — Shay Glenn LLP (57) ABSTRACT

This disclosure is directed to a system and method for detecting a surface of a substrate within a scanner.

16 Claims, 10 Drawing Sheets

(56) References Cited

U.S. PATENT DOCUMENTS

| | | | |
|---|---|---|---|
| 6,517,779 B1* | 2/2003 | Luttermann | B01L 3/021 |
| | | | 422/502 |
| 6,702,990 B1* | 3/2004 | Camacho | B01L 3/0217 |
| | | | 204/613 |
| 6,821,484 B1* | 11/2004 | Gregersen | C12M 47/04 |
| | | | 382/128 |
| 9,593,808 B1* | 3/2017 | Gaitas | B01L 3/0217 |
| 10,012,664 B2 | 7/2018 | Wasson et al. | |
| 2002/0074512 A1 | 6/2002 | Montagu et al. | |
| 2003/0017446 A1* | 1/2003 | Chasse | G01N 1/2806 |
| | | | 435/4 |
| 2003/0085354 A1* | 5/2003 | Fukuda | H01J 37/3056 |
| | | | 250/310 |
| 2003/0179916 A1* | 9/2003 | Magnuson | G01N 33/5005 |
| | | | 382/128 |
| 2003/0194799 A1* | 10/2003 | Achter | B03C 1/288 |
| | | | 435/287.2 |
| 2004/0061049 A1 | 4/2004 | Curry et al. | |
| 2004/0146434 A1* | 7/2004 | Kane | B01L 3/0217 |
| | | | 422/534 |
| 2004/0209382 A1* | 10/2004 | Wakatsuki | G01N 35/0099 |
| | | | 436/177 |
| 2005/0026221 A1* | 2/2005 | Richmond | C12M 33/06 |
| | | | 435/7.2 |
| 2006/0051735 A1* | 3/2006 | Fuhr | G01N 15/14 |
| | | | 435/4 |
| 2006/0121602 A1 | 6/2006 | Hoshizaki et al. | |
| 2006/0257994 A1* | 11/2006 | Noda | B01J 19/0046 |
| | | | 435/287.2 |
| 2007/0071652 A1* | 3/2007 | Cherng | B01L 3/0289 |
| | | | 422/400 |
| 2009/0076650 A1 | 3/2009 | Faes | |
| 2009/0078885 A1* | 3/2009 | Kilper | G02B 21/32 |
| | | | 250/442.11 |
| 2012/0231532 A1 | 9/2012 | Duer | |
| 2013/0105034 A1* | 5/2013 | Gabi | C12M 33/04 |
| | | | 141/1 |
| 2013/0109047 A1* | 5/2013 | Charrier | C12Q 1/24 |
| | | | 435/29 |
| 2013/0280143 A1 | 10/2013 | Zucchelli et al. | |
| 2014/0011226 A1* | 1/2014 | Bernick | C12M 47/06 |
| | | | 435/29 |
| 2014/0125776 A1 | 5/2014 | Damaskinos et al. | |
| 2014/0242570 A1* | 8/2014 | Botma | C12M 47/02 |
| | | | 435/3 |
| 2014/0308163 A1 | 10/2014 | Nordberg et al. | |
| 2014/0338430 A1 | 11/2014 | Theodorsen | |
| 2015/0086971 A1 | 3/2015 | Botma et al. | |
| 2015/0182962 A1 | 7/2015 | Quarre et al. | |
| 2015/0241426 A1 | 8/2015 | Kaldjian et al. | |
| 2015/0247876 A1 | 9/2015 | Quarre et al. | |
| 2015/0274423 A1 | 10/2015 | Borodkin et al. | |
| 2015/0323426 A1* | 11/2015 | Ito | B01L 3/0275 |
| | | | 435/30 |

\* cited by examiner

DETECTING A SUBSTRATE

CROSS-REFERENCE TO RELATED APPLICATIONS

This application is a continuation-in-part of application Ser. No. 14/989,907, filed Jan. 7, 2016, and is a continuation-in-part of application Ser. No. 15/484,925, filed Apr. 11, 2017, which claims the benefit of Provisional Application No. 62/326,502, filed Apr. 22, 2016, and which is a continuation-in-part of application Ser. No. 15/275,416, filed Sep. 25, 2016 (now U.S. Pat. No. 9,810,605), which is a continuation of application Ser. No. 14/248,510, filed Apr. 9, 2014 (now U.S. Pat. No. 9,519,002), which claims the benefit of Provisional Application No. 61/810,834, filed Apr. 11, 2013, and Provisional Application No. 61/922,931, filed Jan. 2, 2014.

TECHNICAL FIELD

This disclosure relates generally to detecting a substrate, though more specifically, to detecting a slide surface within a scanner.

BACKGROUND

A picker or picking system may be used to isolate a target analyte from a suspension in or on a substrate, such as a well plate, a slide, a tube, or the like, or to draw a fluid, such as a, suspension, solution or reagent, from the substrate. As a result, practitioners, researchers, and those working with suspensions continue to seek systems and methods to more efficiently and accurately detect a substrate surface.

DETAILED DESCRIPTION

This disclosure is directed to a system and method for detecting a surface of a substrate within a scanner.

In the following description, the term "sample" is used to describe biological fluid, a biological semi-solid, a biological solid (which may remain solid, such as tissue, or may be liquefied in any appropriate manner), a suspension, a portion of the suspension, a component of the suspension, or the like. For example, for anticoagulated whole blood, the sample may be the anticoagulated whole blood (i.e. a suspension), the buffy coat (i.e. a portion of the suspension), or a circulating tumor cell (i.e. a component of the suspension). For the sake of convenience, the sample referenced is whole blood, though it should be understood that the method and system described and discussed herein may be used with any appropriate sample, such as urine, blood, bone marrow, buffy coat, cystic fluid, ascites fluid, stool, semen, cerebrospinal fluid, nipple aspirate fluid, saliva, amniotic fluid, vaginal secretions, mucus membrane secretions, aqueous humor, vitreous humor, vomit, and any other physiological fluid or semi-solid. For example, the sample may be a tissue sample or a material from adipose tissue, an adrenal gland, bone marrow, a breast, a caudate, a cerebellum, a cerebral cortex, a cervix, a uterus, a colon, an endometrium, an esophagus, a fallopian tube, a heart muscle, a hippocampus, a hypothalamus, a kidney, a liver, a lung, a lymph node, an ovary, a pancreas, a pituitary gland, a prostate, a salivary gland, a skeletal muscle, skin, a small intestine, a large intestine, a spleen, a stomach, a testicle, a thyroid gland, a bladder, or a vagina.

In the following description, the term "target analyte" is used to describe a biological material included within the sample which may be collected, imaged, characterized, evaluated, enumerated, analyzed, or the like. It should also be understood that the target analyte can be a fraction of a sample, such as buffy coat, a cell, such as ova, fetal material (such as trophoblasts, nucleated red blood cells, fetal red blood cells, fetal white blood cells, fetal DNA, fetal RNA, or the like), a circulating tumor cell ("CTC"), a circulating endothelial cell, an immune cell (i.e. naïve or memory B cells or naïve or memory T cells), a vesicle, such as an exosome, a liposome, a protein, a nucleic acid, a biological molecule, a naturally occurring or artificially prepared microscopic unit having an enclosed membrane, parasites (e.g. spirochetes, such as *Borrelia burgdorferi* which cause Lyme disease; malaria-inducing agents), microorganisms, viruses, or inflammatory cells. For example, the target analyte may be a tumor cell from adipose tissue, an adrenal gland, bone marrow, a breast, a caudate, a cerebellum, a cerebral cortex, a cervix, a uterus, a colon, an endometrium, an esophagus, a fallopian tube, a heart muscle, a hippocampus, a hypothalamus, a kidney, a liver, a lung, a lymph node, an ovary, a pancreas, a pituitary gland, a prostate, a salivary gland, a skeletal muscle, skin, a small intestine, a large intestine, a spleen, a stomach, a testicle, a thyroid gland, a bladder, or a vagina.

In the following description, the term "substrate" is used to describe a surface or vessel, such as for collecting, holding, storing, or transporting a sample or target analyte. The substrate may be, but is not limited to, a well plate, a slide (such as a microscope slide), or a tube (such as an Eppendorf tube, a microtainer, a standard tube, or a collection tube). The substrate may be composed of glass, crystal, plastic, metal, organic or inorganic materials, polyoxymethylene ("Delrin®"), polystyrene, acrylonitrile butadiene styrene ("ABS") copolymers, aromatic polycarbonates, aromatic polyesters, carboxymethylcellulose, ethyl cellulose, ethylene vinyl acetate copolymers, nylon, polyacetals, polyacetates, polyacrylonitrile and other nitrile resins, polyacrylonitrile-vinyl chloride copolymer, polyamides, aromatic polyamides ("aramids"), polyamide-imide, polyarylates, polyarylene oxides, polyarylene sulfides, polyarylsulfones, polybenzimidazole, polybutylene terephthalate, polycarbonates, polyester, polyester imides, polyether sulfones, polyetherimides, polyetherketones, polyetheretherketones, polyethylene terephthalate, polyimides, polymethacrylate, polyolefins (e.g., polyethylene, polypropylene), polyallomers, polyoxadiazole, polyparaxylene, polyphenylene oxides ("PPO"), modified PPOs, polystyrene, polysulfone, fluorine containing polymer such as polytetrafluoroethylene, polyurethane, polyvinyl acetate, polyvinyl alcohol, polyvinyl halides such as polyvinyl chloride, polyvinyl chloride-vinyl acetate copolymer, polyvinyl pyrrolidone, polyvinylidene chloride, specialty polymers, polystyrene, polycarbonate, polypropylene, acrylonitrite butadiene-styrene copolymer, or combinations thereof. The substrate may be optically clear, translucent, or opaque. The substrate may be charged, such as positively or negatively. The substrate may include a coating such as pluronic, siliconizing reagent (e.g. Sigmacote®), or the like.

In the following description, the term "external device" is used to describe a device external to the scanner which may be in communication with the scanner, such as by a wireless or wired connection, to provide instructions, to input and/or retrieve information, store and/or transmit data, and/or control the scanner. The external device may include, but is not limited to, a computer, a tablet, a phone, a PDA, or a handheld device.

In the following description, the term "detection moiety" is used to describe a compound or substance which provides a signal for detection, thereby indicating the presence of another compound or substance, an analyte, or the like within a sample or specimen. The detection moiety may be fluorescent, such as a fluorescent probe, or chromogenic, such as a chromogenic dye.

General Description of a Scanner and Subsystem

Figure 1A:
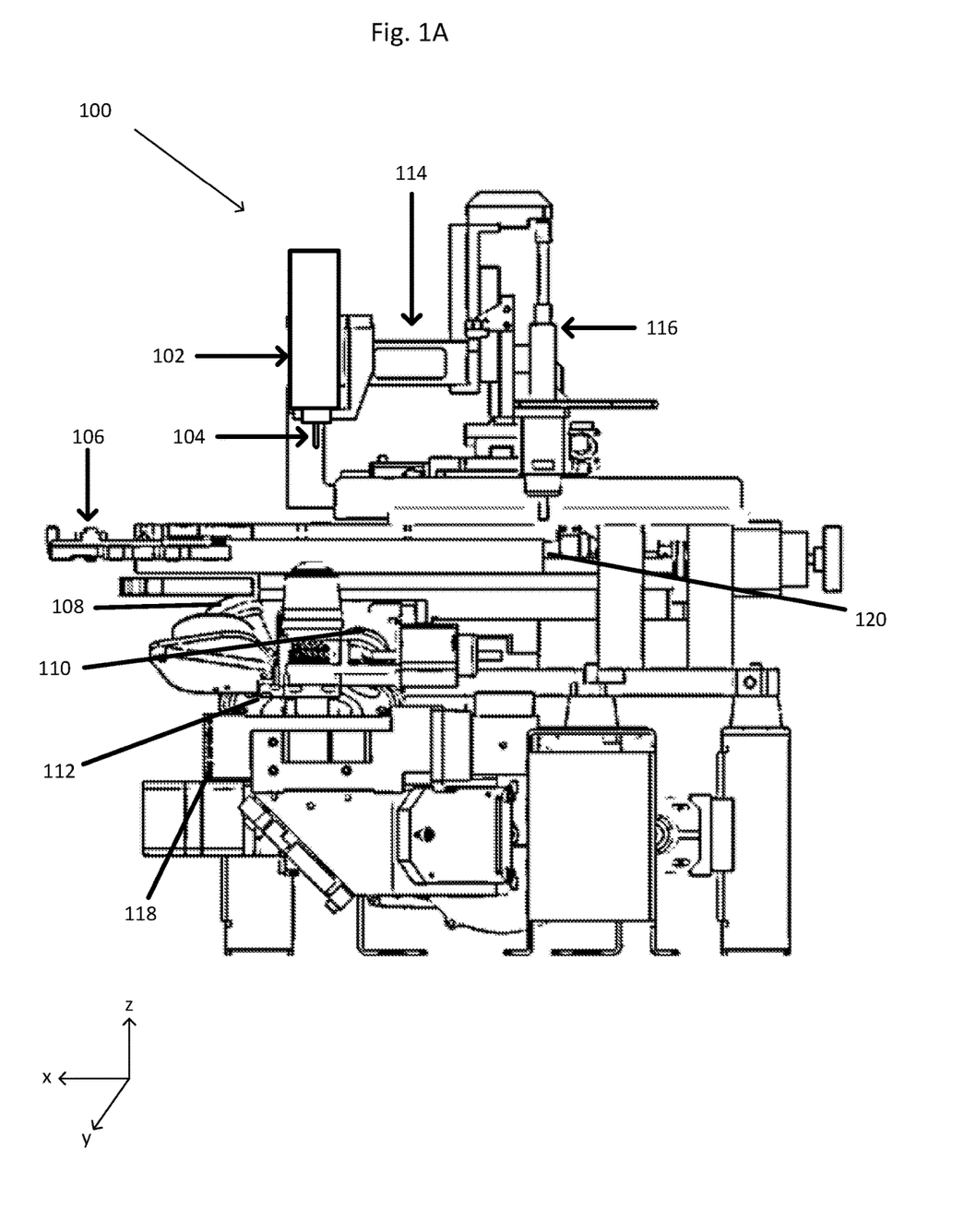
FIG. 1A shows an example scanner.
Figure 1B:
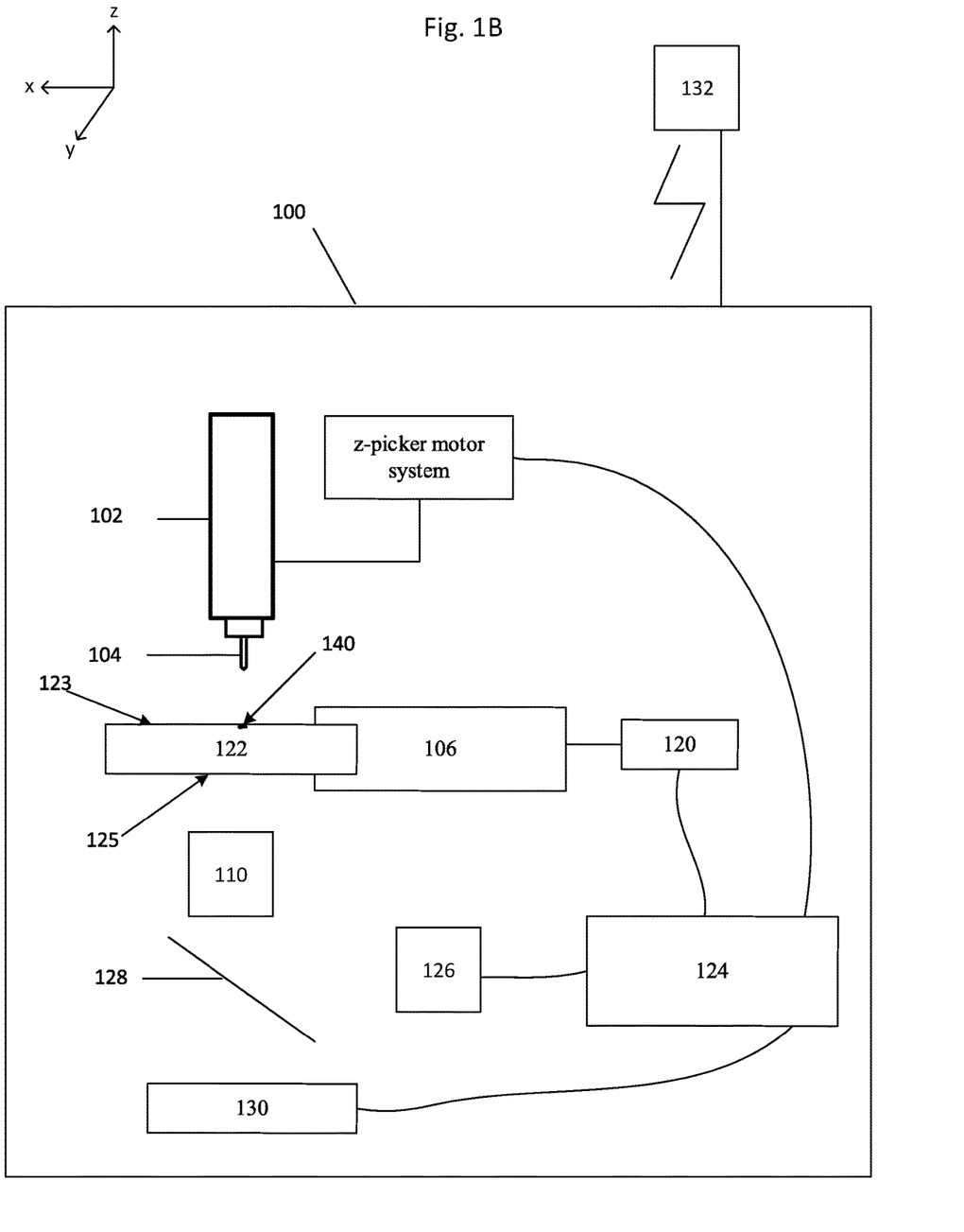
FIG. 1B shows a block diagram of the example scanner connected to an example external device.

FIG. 1A shows an isometric view of a scanner 100 with a cover removed. FIG. 1B shows a block diagram of the scanner 100. The scanner 100 includes a picker 102 having a picker tip 104. The picker 102 is a device for isolating a target analyte 140 or target material from the remainder of a sample. The picker 102 may be driven along the z-axis by a z-picker motor system, which may include at least one of a coarse z-motor 116 and a fine z-motor 114.

The picker tip 104 may be stiff, flexible, or formable. The picker tip 104 may be straight, angled, curved, hooked, or any appropriate shape or configuration. The picker tip 104 may be non-clogging.

The picker tip 104 can also be composed of a variety of different materials including, but not limited to, ceramics; glass; metals; organic or inorganic materials; plastic materials; polymers; jewels (i.e. ruby, sapphire, or diamond); and combinations thereof. Furthermore, the picker tip 104 may be composed of a material that is fluorescent. Additionally, the picker tip 104 may be impact-resistant, hard, and dimensionally stable (i.e. axially and/or torsionally stiff). The picker tip 104 may have a density that is greater than or equal to 2.0 g/cc. The picker tip 104 may have a hardness that is greater than or equal to 5 Vickers. The picker tip 104 may have a Modulus of Elasticity that is greater than or equal to 17 GPa.

The picker tip 104 includes a first end inserted into the picker 102 and a second end extending away from the picker 102. The second end includes an opening to access a central bore. An inner portion of the second end includes a straight wall extending from the opening into the central bore. A curved wall extends from the straight wall further into the central bore. An angled wall extends from the curved wall further into the central bore. An upper wall extends from the angled wall further into the central bore. In other words, the central bore has a first diameter that is substantially equal to the diameter of the opening, which then increases in diameter along the curved wall and the angled wall until reaching the upper wall, whereby the diameter may remain constant or increase along a taper. The diameter of the opening and the straight wall may be less than or equal to 1 micrometer or less than or equal to 1 millimeter. The radius of the curved wall may be approximately 25 micrometers to 2.6 millimeters. The diameter of the central bore where the angled wall connects to the upper wall may be approximately 125 micrometers to approximately 2.6 millimeters. The second end may be sharpened, thereby having an outer wall that has an angle from the horizontal that may range from approximately 30° to approximately 89°. The sharpened second end permits for better cutting of the desired target analyte 140 from a substrate 122. The angle of the outer wall permits selection of the desired target analyte 140 without destroying any other analytes, whether target or non-target.

The scanner 100 also includes a substrate holder 106 for holding and supporting the substrate 122 that includes the sample, such as buffy coat, or a fluid, such as a reagent. The scanner 100 may also include a turret 112, including a first objective 110 and a deflection detector 108 (to measure the deflection of the substrate, when it is desirous to do so), which rotates to bring the first objective 110 and the deflection detector 108 underneath the substrate 122 when it is desirous to do so. The turret 112 may include more than one objective, each objective having different magnification levels, when it is desirous to do so. The deflection detector 108 may be tactile (i.e. touch or pressure sensor), capacitive, optical, acoustic (i.e. sound) or the like. A z-axis turret motor 118 drives the turret 112 along the z-axis, such as towards and away from the substrate or substrate holder 106.

In one embodiment, the picker 102 may be located on a first side of the substrate holder 106 or a first side 123 of the substrate 122 and the detector 130 and at least one light source 126 may be located on a second side of the substrate holder 106 or a second side 125 of the substrate 122 (i.e. different, opposite, or opposing sides). In one embodiment, the picker 102, the detector 130, and the at least one light source 126 may be located on the same side of the substrate holder 106 or the substrate 122.

A slide motor 120 may be activated to move the substrate holder 106, thereby moving the substrate 122, horizontally or orthogonally. The picker 102 may be connected to the z-picker motor system, which may include a coarse z-motor 116 and a fine z-motor 114. The fine z-motor 114 may be a vibration-inducing component (i.e. a voice coil, an ultrasonic transducer, or the like), may be a drive component that moves in approximately 1-20 μm steps, or a combination thereof to induce vibration and drive the picker tip 104 (i.e. a piezoelectric motor or the like).

Figure 2A:
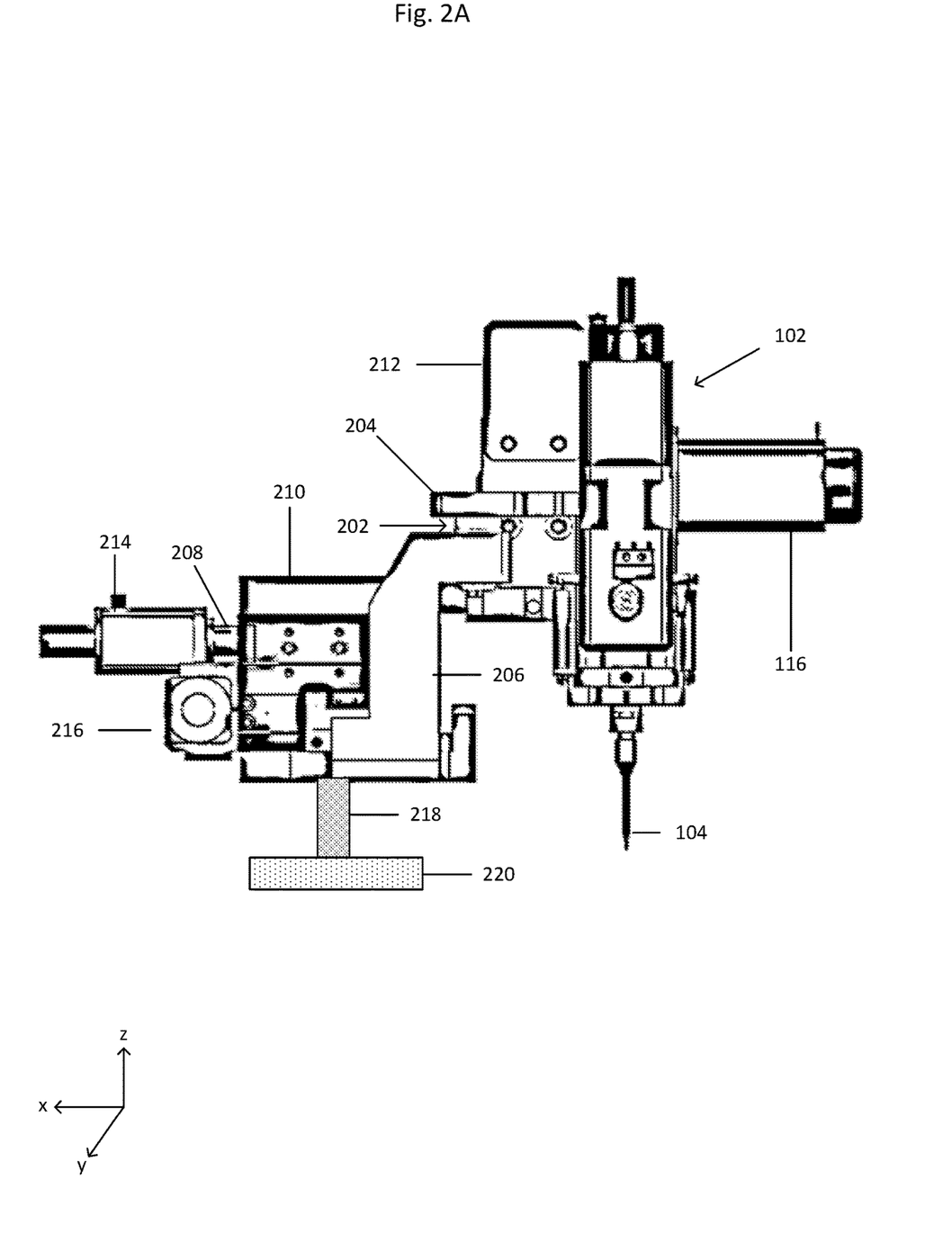
FIGS. 2A-2B show an example subsystem of the scanner.
Figure 2B:
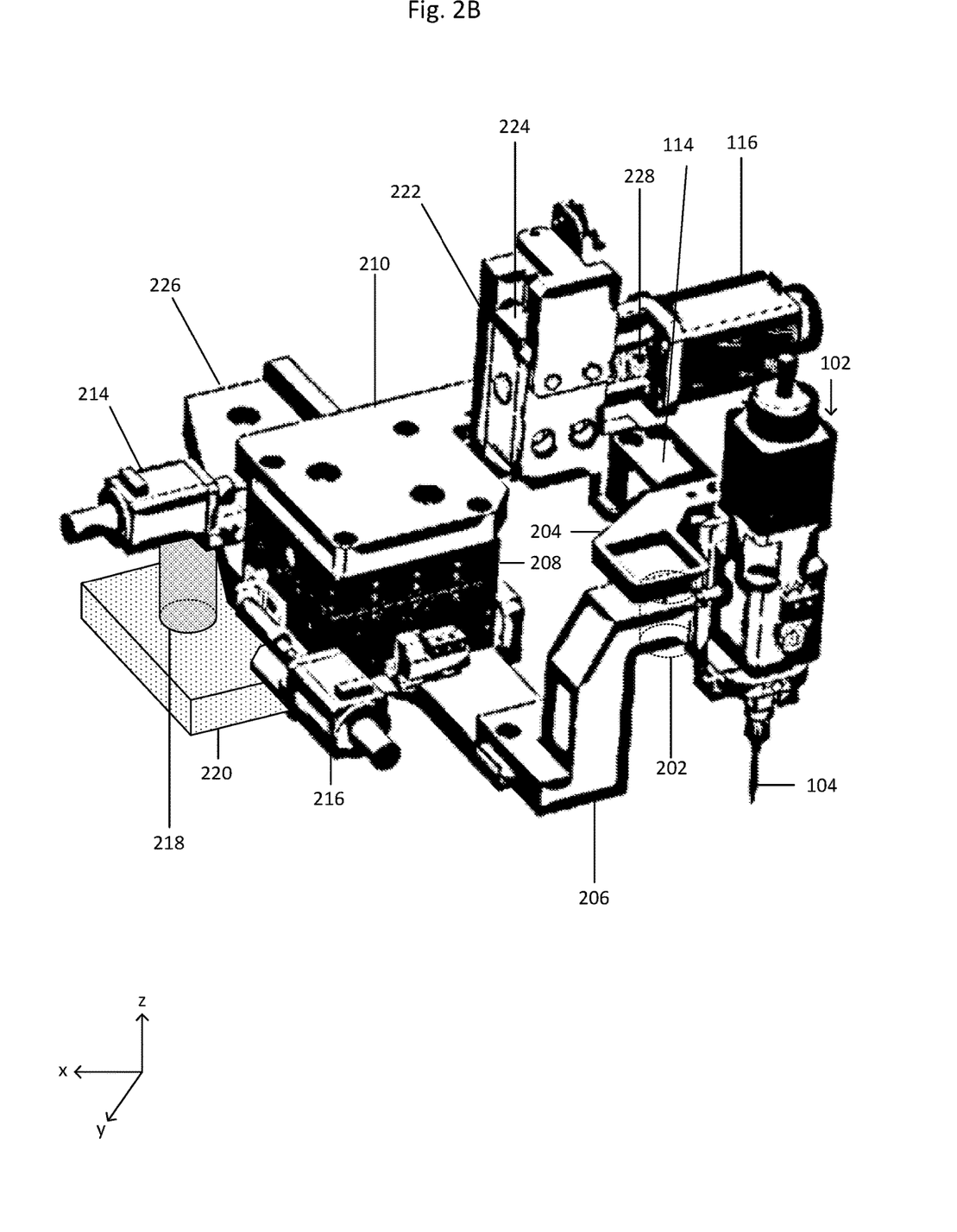

FIGS. 2A and 2B show a subsystem 200 of the picking and imaging system shown in FIG. 1A. FIG. 2A shows a front view of the subsystem 200 and the FIG. 2B shows an isometric view of the subsystem 200. The subsystem 200 includes a position detector including a sensor 202 and a target plate 204. The sensor 202 may be mechanical (switch), electrical (linear encoder), capacitive, optical (laser), acoustic, inductive (linear variable differential transformer), or the like. The subsystem 200 also includes the picker 102 including the picker tip 104; and may also include the substrate holder 106 to support a substrate. In one embodiment, the substrate holder 106 may be a fixed z-distance from the sensor 202 and the target plate 204 may be a fixed z-distance from the picker tip 104. The picker tip 104 and the target plate 204 may be moveable along the z-axis relative to the substrate holder 106 and the sensor 202, respectively. Furthermore, the target plate 204 may be fixedly attached to the picker 102, whether directly (i.e. being mounted to a component of the picker 102) or indirectly (i.e. being mounted to a plate or bracket attached to the picker 102). The subsystem 200 may also include a reference plate 220, which may be a fixed z-distance from at least one of the sensor 202 and the substrate holder 106. The subsystem 200 also includes a z-picker motor system, wherein the target plate 204 and the picker 102 are driven along the z-axis by the z-picker motor system. The z-picker motor system may include at least one of the coarse z-motor 116 and the fine z-motor 114. The fine z-motor 114 may be a piezoelectric motor. The fine z-motor 114 has a travel range of approximately 0.001-500 µm and the coarse z-motor 116 has a travel range of approximately 1-50 mm. Additionally, the z-picker motor system may include a vibration-inducing component to cause the picker 102 to oscillate along the z-axis. The vibration-inducing component may be a voice coil, an ultrasonic transducer, or a piezoelectric motor. The picker 102 may oscillate at a frequency less than or equal to approximately 10 kHz and have an amplitude of approximately 1-20 µm.

In one embodiment, the substrate holder 106 may be a fixed z-distance from the target plate 204 and the sensor 202 may be a fixed z-distance from the picker tip 104.

The voltage output of the position detector is amplified by an amplifier and then input into a controller board which provides a second output voltage and fed back to the z-picking motor system. The z-picker motor system may then adjust the distance between the sensor 202 and the target plate 204 to a desired distance based on the second voltage output from the controller board. The distance and second output voltage relationship may have already been calibrated, such that the second output relates to a known distance whereby driving the target plate 204 towards or away from the sensor 202 and determining the second output voltage provides the desired distance. For example, when the second output voltage is 1.0 V, the target plate 204 and the sensor 202 may be 1 mm away from one another. However, when the desired distance is 2 µm, and it is known that the second voltage output is 3.1 V when the target plate 204 and the sensor 202 are 2 µm away from one another, the target plate 204 may be driven towards the sensor 202 until the second output voltage is 3.1 V.

The picker 102 may be connected to an x-y stage 208 such as by an x-y connector plate 210. The x-y stage 208 may be connected to an x-axis motor 216, a y-axis motor 214, and a base plate 226. The base plate 226 may be connected to a reference plate 220 by at least one post 218. The reference plate 220 is stationary and acts as a point or plane against which movement in the x-, y-, and z-axes may be referenced. The reference plate 220 may be mounted on vibration plates (not shown) within the scanner to inhibit the influence of vibration, whether external or internal to the picker 102, on movement and control of the picker 102. The sensor 202 may be connected to the base plate 226 by a sensor mount 206.

The coarse z-motor 116 may be connected to the picker 102 by a coupling 228. The coupling 228 may also be connected to a coarse z-stage carriage 224. A coarse z-stage base 222 may act as a guide for the coarse z-stage carriage 224 and may also include a stop 212 to limit the furthest travel of the coarse z-motor 116 relative to the substrate holder 106.

Figure 2C:
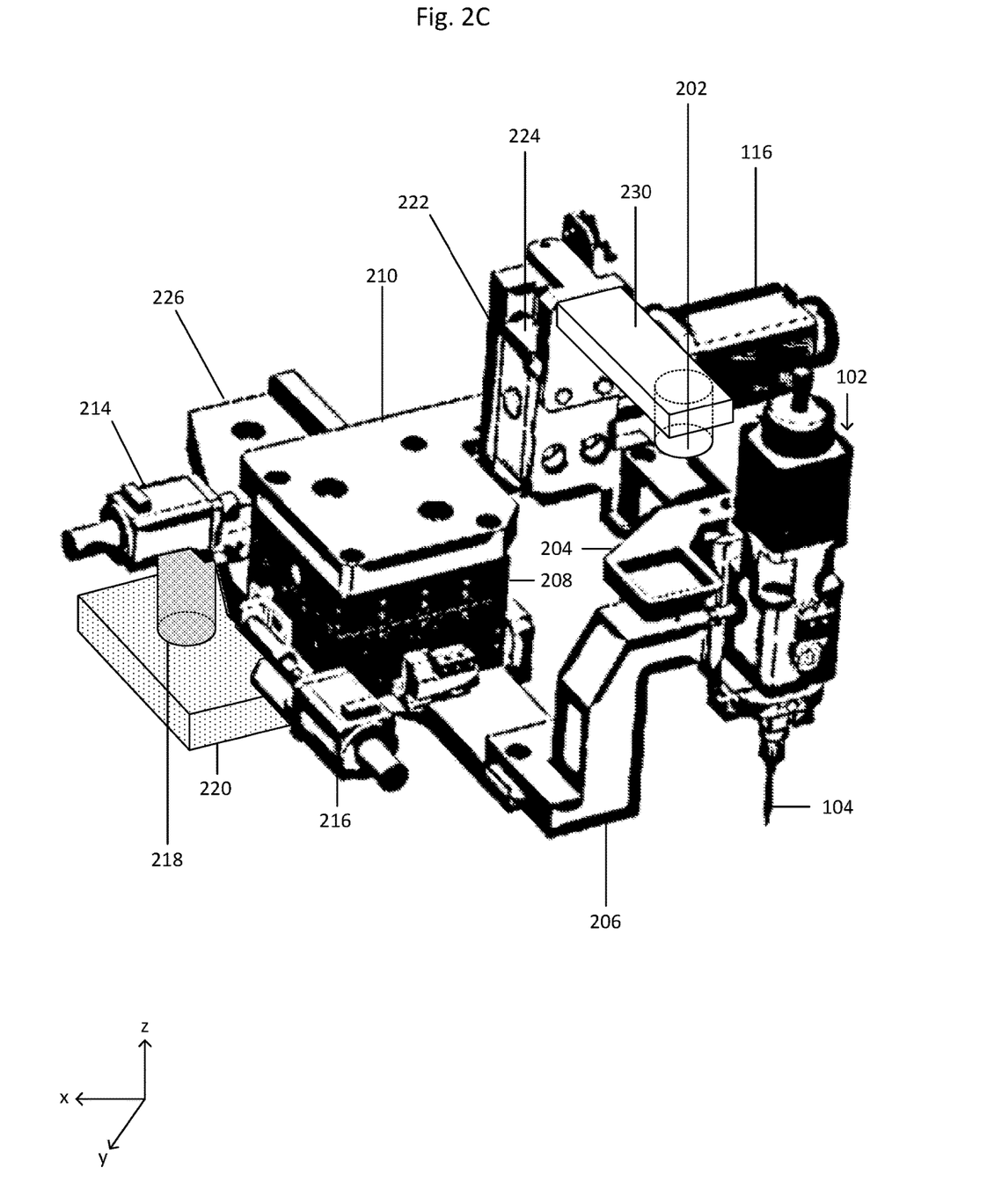
FIG. 2C shows an example subsystem of the scanner.

FIG. 2C shows a subsystem of the scanner 100. The subsystem of FIG. 2C is similar to the subsystem of FIG. 2B except that the sensor 202 is fixed in a different location relative to the target plate 204, such as with a bracket 230. In one embodiment, the substrate holder 106 may still be a fixed z-distance from the sensor 202 and the target plate 204 may still be a fixed z-distance from the picker tip 104. However, when the picker 102 is driven towards the substrate holder 106, the target plate 204 moves away from the sensor 202. In one embodiment, the substrate holder 106 may still be a fixed z-distance from the target plate 204 and the sensor 202 may still be a fixed z-distance from the picker tip 104. However, when the picker 102 is driven towards the substrate holder 106, the sensor 202 moves away from the target plate 204. The voltage or current outputs are calibrated and adjusted to account for one of the sensor 202 or the target plate 204 moving anyway from the other one, as compared to one of the sensor 202 or the target plate 204 moving toward the other one.

Substrate Detection

In one embodiment, a method for locating a surface of a substrate includes driving the picker 102 including the picker tip 104 from a holding position towards and at least partially past the substrate holder 106. Alternatively, the picker 102 including the picker tip 104 may be driven from a holding position towards a substrate without touching or going past the substrate, such that the holding position is above the substrate. During the driving step, a first output is obtained by the position detector. The picker 102 including the picker tip 104 is then returned or withdrawn to the holding position. A substrate 122 is then inserted into the substrate holder 106. The picker 102 including the picker tip 104 is then re-driven from the holding position towards the substrate until the picker tip at least touches the substrate. During the re-driving step, a second output is obtained by the position detector.

After contact, the picker 102 including the picker tip 104 overtravel until a threshold is reached. The substrate 122 may be located by calculating the difference between the first output and the second output, such as a point where the difference is equal to or greater than the threshold (such as 250 ADC counts) or at the point at which the first and second outputs are not equal. The first and second outputs may be plotted, stored in memory, or any appropriate manner of retaining the data for subsequent comparison, analysis, and/or use. The first and second outputs may be voltage, current, or the like.

Though the subsystem above is discussed as being driven along the z-axis, the subsystem may be driven along one of the x-, y-, or z-axes, whether based on orientation or an appropriate layout. For example, when the subsystem drives along the z-axis, the holding position may above or below the substrate holder 106.

Figure 3:
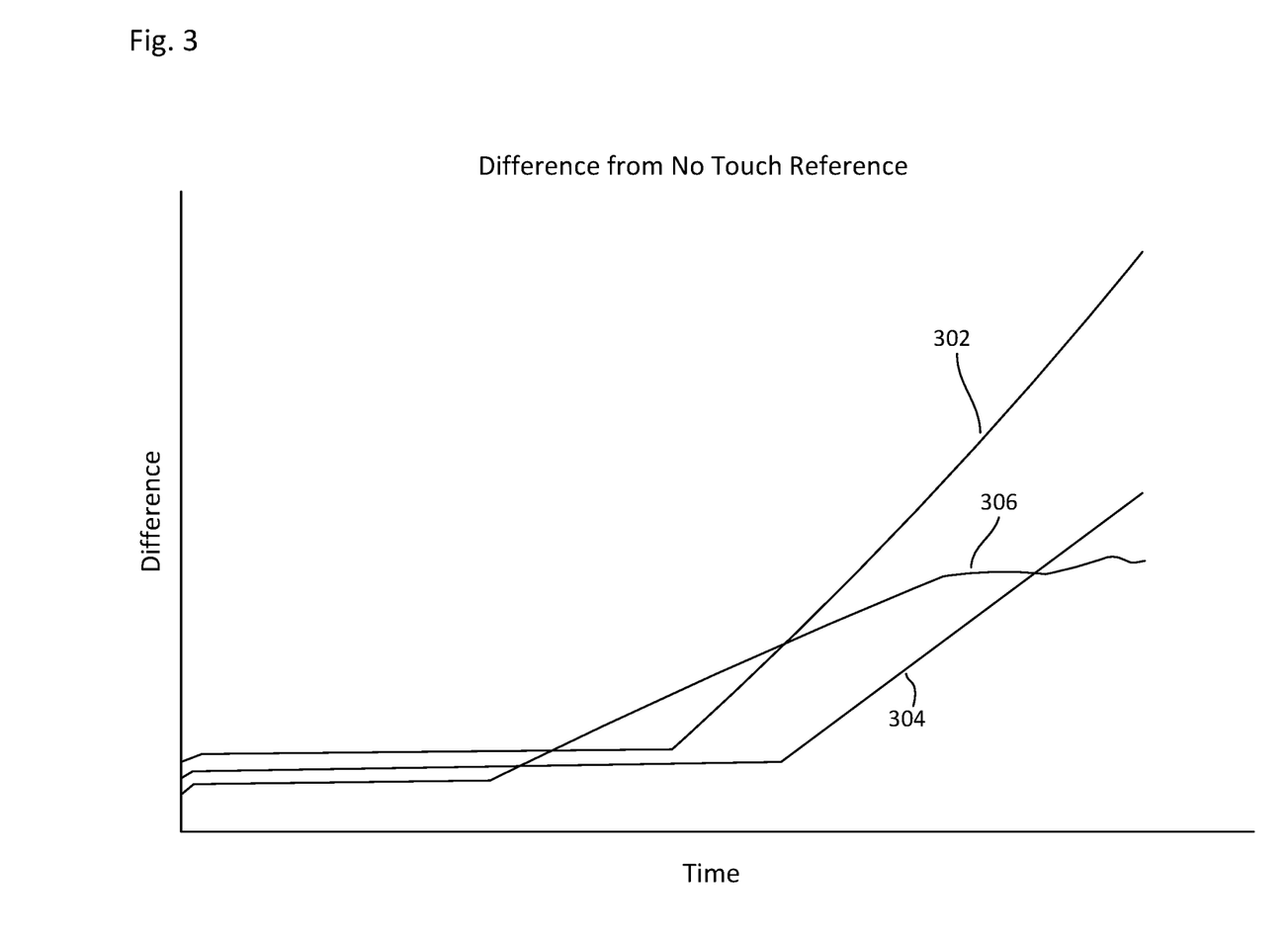
FIG. 3 shows a second output obtained at three different locations on a substrate.

FIG. 3 shows the second output obtained at three different locations on the substrate. Line 302 shows the second output when the picker 102 including the picker tip 104 touches a portion of the substrate being the stiffest, which may be the middle section. Line 304 shows the second output when the picker 102 including the picker tip 104 touches a portion of the substrate having a medium stiffness. Line 306 shows the second output when the picker 102 including the picker tip 104 touches a portion of the substrate having the least stiffness. In the example provided, the movement of the break points in the lines 302, 304, 306 may be due to the slope of the substrate. The break point(s) may be the surface of the substrate at the respective points.

Figure 4A:
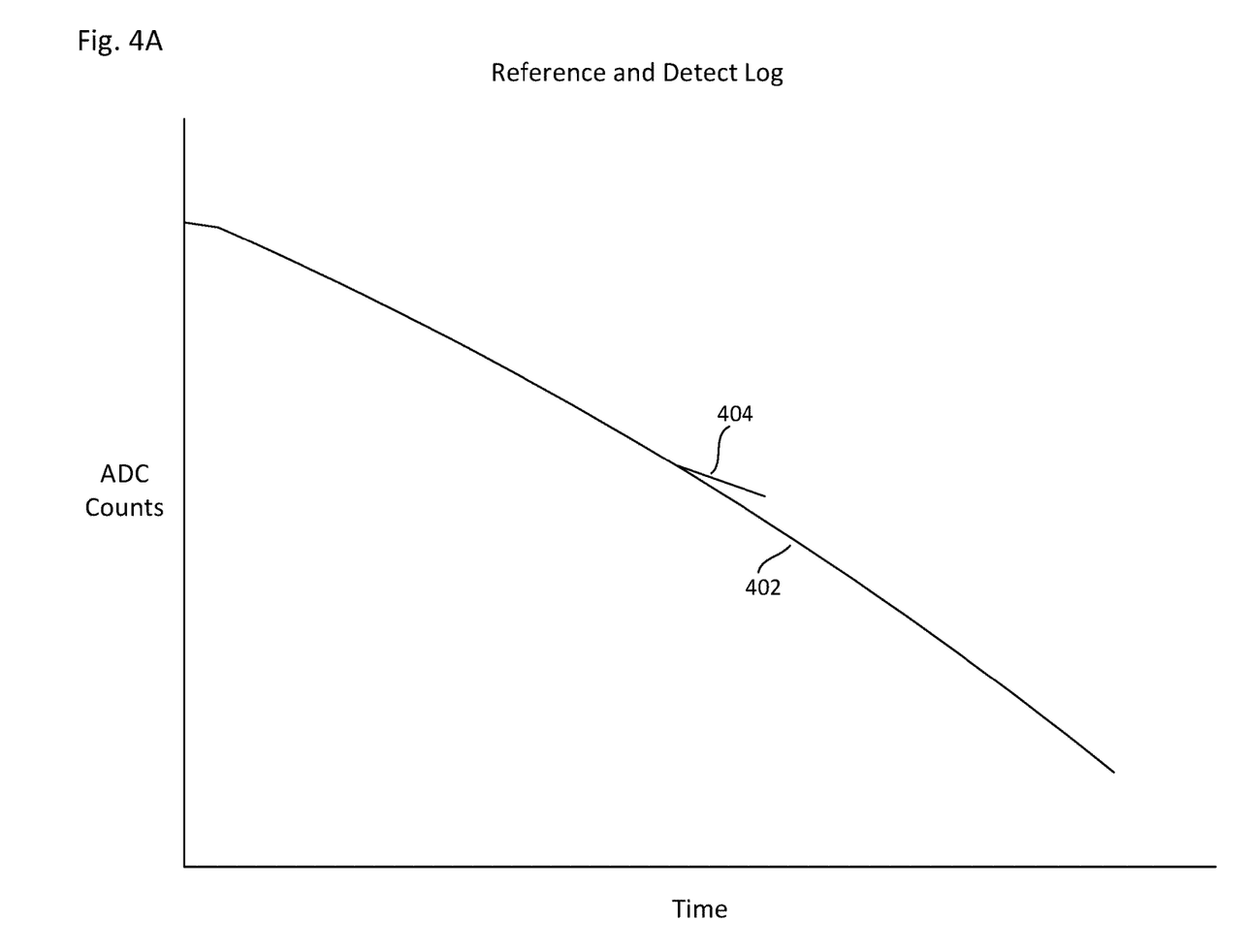
FIG. 4A shows a first output and a second output superimposed.
Figure 4B:
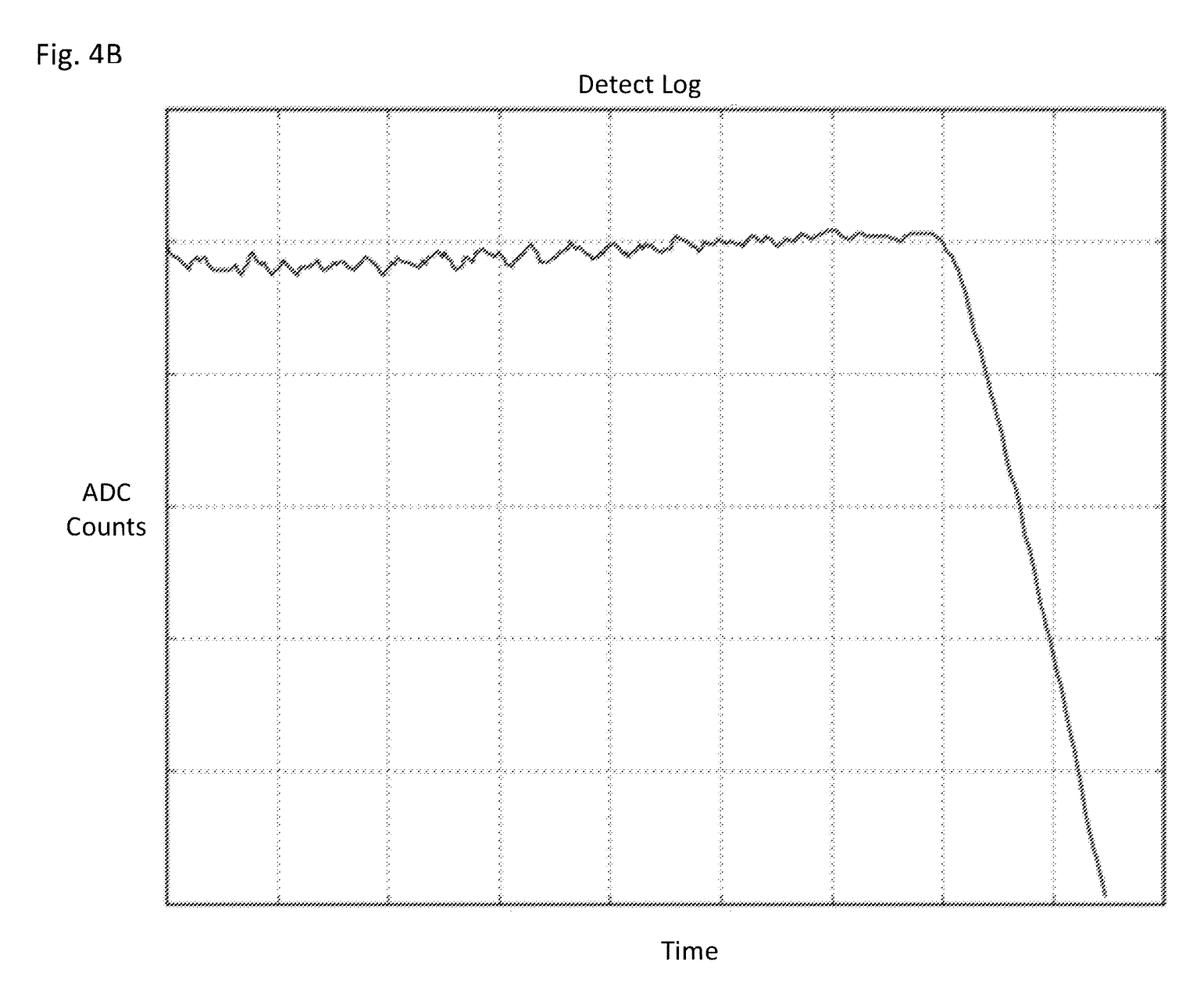
FIG. 4B shows the difference between the first output and the second output of FIG. 4A.

FIG. 4A shows a first output 402 and a second output 404 superimposed. The point at which the second output 404 splits from the first output is where the substrate is touched by the picker 102 including the picker tip 104. FIG. 4B shows the difference between the first output 402 and the second output 404. In this case, the detect algorithm has been completed when the difference exceeds a threshold, such as 250 ADC counts, during overtravel. Movement and logging data are stopped as well.

In one embodiment, a method for locating a surface of a substrate includes driving the picker 102 including the picker tip 104 from a holding position towards the substrate holder 106. During the driving step, the picker 102 including the picker tip 104 is moved in steps, for example, from a first position to a second position. A known output is determined based on the movement of the picker 102 from the first position to the second position. The picker 102 including the picker tip 104 is then commanded to be moved from the second position to a third position. However, the picker 102 including the picker tip 104 does not travel the full distance in moving from the second position to the third position.

Figure 5A:
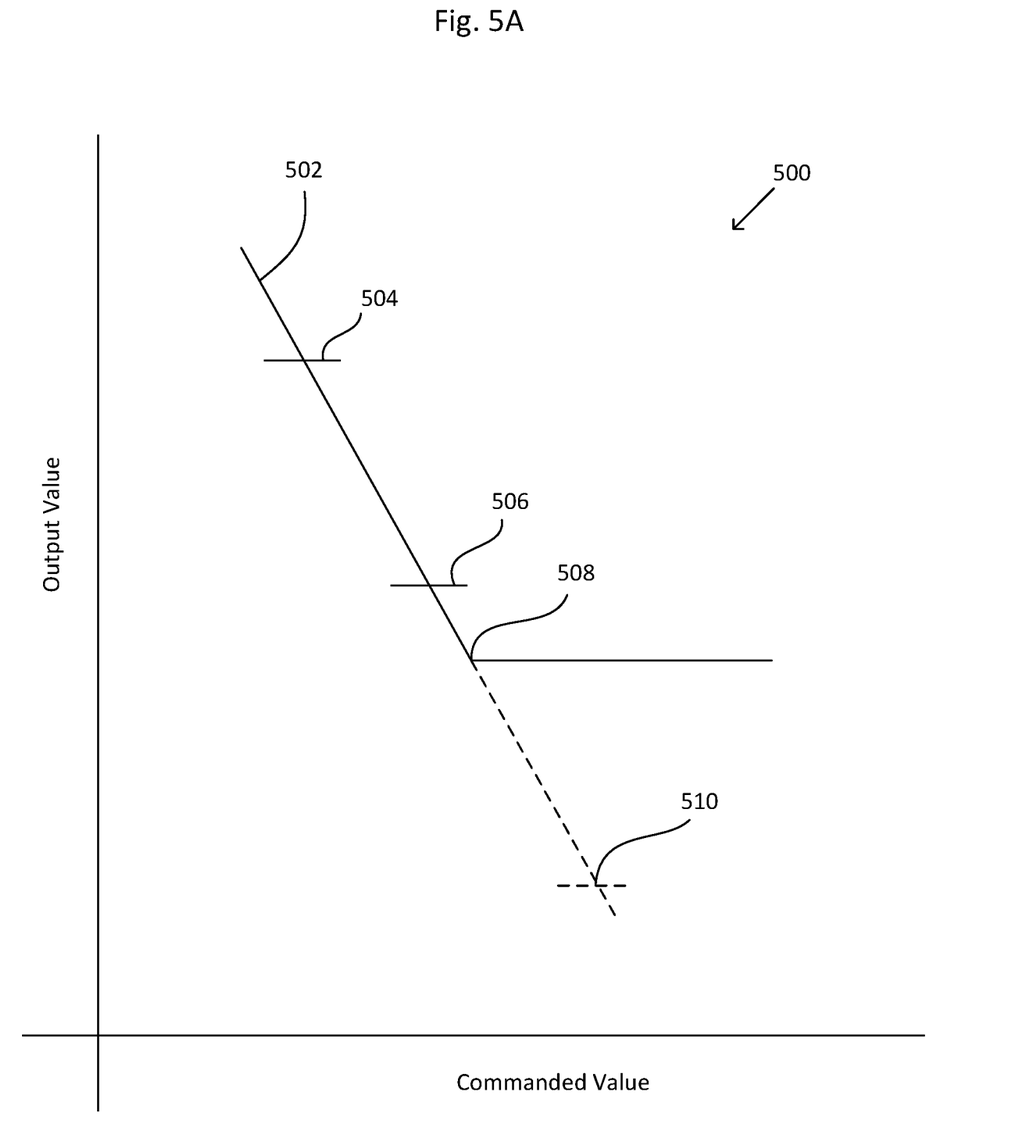
FIGS. 5A-5B show outputs.

FIG. 5A shows an actual output 502 superimposed with an expected output (the dashed line). The picker 102 including the picker tip 104 moves from a first position 504 to a second position 506. The picker 102 including the picker tip 104 is then commanded to move from the second position 506 to a third position 510. As the picker 102 is commanded to move to the third position 510, the values obtained from the position detector are expected to follow the dashed line, thereby resulting in the value of the third position 510. However, during travel, the picker 102 touches the substrate and the output therefore deviates from the expected value. After contact, the picker 102 including the picker tip 104 overtravels until a threshold is reached. The substrate 122 may be located by calculating the difference between the actual output and the expected output, such as a point where the difference is equal to or greater than the threshold or at the point at which the actual and expected outputs are not equal.

Figure 5B:
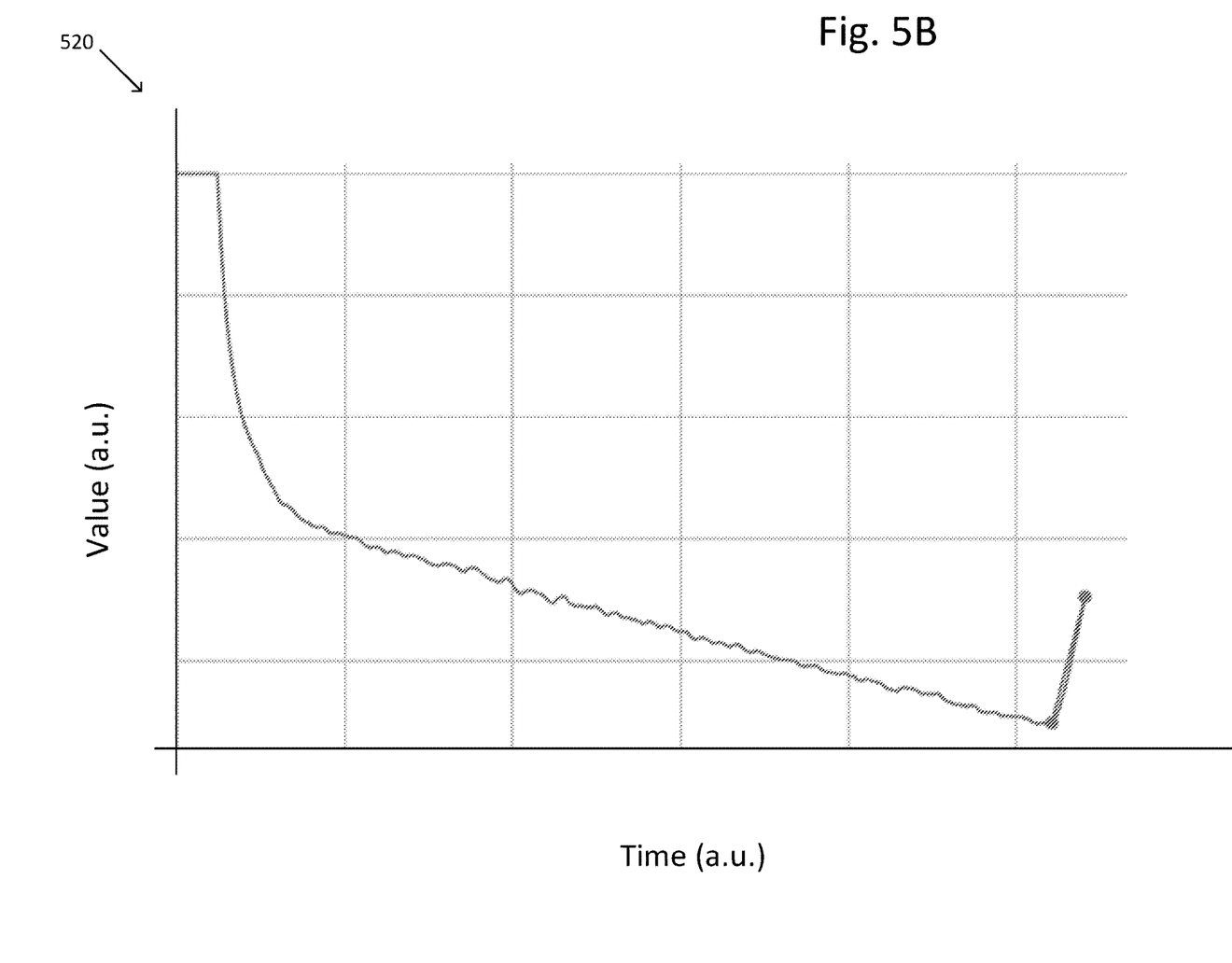

In one embodiment, a method for locating a surface of a substrate, such as method 520 of FIG. 5B, includes driving the picker 102 including the picker tip 104 from a holding position towards and at least partially past the substrate holder 106. During the driving step, mathematical computations, such second order derivatives or the like, are performed on the at least one output value obtained by the position detector to obtain a negative slope. Upon the picker 102 including the picker tip 104 contacting the substrate, a change in slope, from negative to positive, is achieved during contact. After contact, and during at least some overtravel, a certain number of positive slope values are obtained. Once a given number of positive slope values are obtained, the overtraveling may stop and the location of the substrate surface may be determined. The given number of positive slope values may be any appropriate number including up to 10,000, such as up to 1, 5, 10, 20, 25, 50, 75, 100, 150, 200, 250, 300, 400, 500, 750, 1000, 1100, 1200, 1500, 2000, 2500, 5000, or 7500. In one embodiment, the initial slopes obtained may be positive and then slopes after contact may be negative.

Overtravel is the continued driving of the picker 102 including the picker tip 104 even after the picker 102 including the picker tip 104 has contacted the substrate. Overtravel may be a step performed after the at least two steps of driving and contacting. After at least contacting, the substrate may be overtraveled by up to 1 millimeter, including such distances as 1, 3, 5, 7, or 10 μm. In one embodiment, overtravel may cause the substrate to deflect. In one embodiment, overtravel may not cause the substrate to deflect.

The picker tip 104 exerts a force on the substrate during the overtravel step. The force exerted may cause the substrate to deflect without causing the substrate to slip out of the substrate holder, become misaligned, crack, or break. In one embodiment, the picker tip 104 may exert a force of 0.01-16 ounces on the substrate during the overtravel step. In one embodiment, the picker tip 104 may exert a force of 1-2 ounces on the substrate during the overtravel step. In one embodiment, the picker tip 104 may exert a force of 4 ounces on the substrate during the overtravel step.

Method

To obtain a sample including at least one target analyte, the sample may be withdrawn directly from a subject, such as by venipuncture, or the sample may undergo enrichment and/or isolation from a suspension. The sample may be enriched by any appropriate enrichment process including, but not limited to, density-based separation, sequential density fractionation, magnetic-activated cell sorting, fluorescence-activated cell sorting, differential lysis, depletion filters, or the like. Sequential density fractionation is a process by which a suspension is divided into fractions or a fraction of a suspension is divided into sub-fractions by a step-wise or sequential process, such that each step or sequence results in the collection or separation of a different fraction or sub-fraction from the preceding and successive steps or sequences. The sample may be obtained from other suspension components by selecting the sample with a device for picking, such as a cell picker, a pipet, a syringe, or the like.

After obtaining the sample, the sample may be placed on or in a substrate. In one embodiment, the substrate is a microscope slide having a first side including the sample or target analyte and a second side being blank or empty. Furthermore, the sample may be adhered to the substrate, such as with an attachment solution. For example, the sample may be re-suspended in the attachment solution. Alternatively, the attachment solution may be added to or mixed with the sample. The re-suspended sample, which includes at least a portion of the attachment solution is dispensed onto or into the substrate by a dispenser, such as a pipet or repeating pipet, and spread across the substrate. The sample, where appropriate, may then be spread across the substrate by a spreader, such as a squeegee, a pipet tip, a blade, a two-piece spreader including a blade and a base. Alternatively, the sample may be spread across the substrate by centrifuging, wetting, or nutating the substrate. The re-suspended sample is cured to adhere the re-suspended sample to the substrate. Alternatively, the re-suspended sample may be dispensed onto the substrate and cured without being spread across the substrate. Curing may occur in air, such as at room temperature; in an environmentally-controlled chamber, such as at 37° C.; or the like. Furthermore, the sample may undergo an additional fixation step, such as in formalin or any appropriate fixative, after the curing step has been completed.

The target analyte and a non-target analyte may have a number of different types of molecules located on the surface or within the analyte. Each type of receptor is a molecule capable of attaching a particular linking molecule. As a result, linking molecules can be used to classify the target analytes and/or non-target analytes and determine the specific type of target analytes and/or non-target analytes present in the suspension by binding linking molecules that attach to particular receptors with a particular detection moiety. The analytes may be classified based on various markers including nuclear markers, intracellular markers, extracellular markers (such as a membrane marker), and exclusion markers. For example, each type of detection moiety emits light in a narrow wavelength range of the electromagnetic spectrum when an appropriate stimulus, such as light with a shorter wavelength, is applied. A first detection moiety that emits light having a wavelength in the green channel can be attached to a first linking molecule that binds specifically to a first type of receptor, while a second detection moiety that emits light having a wavelength in the red channel can be attached to a second linking molecule that binds specifically to a second type of receptor. The color observed, based on the wavelength emitted, as a result of stimulating the respective detection moiety identifies the type of receptor, and because receptors can be unique to particular target analytes and/or non-target analytes, the color can also be used to identify the target particle. This allows for detection of multiple receptors on the target material at any given time.

A stain is compound for labeling a biological material which includes a detection moiety and the linking molecule. The detection moiety is a compound which provides a signal, such as by emission or blocking, when exposed to a stimulus, such as light or electromagnetic radiation. The detection moiety may be used as a tracer, as a label for certain structures, as a label for biomarkers, or the like. The detection moiety can be distributed or can label the appropriate structure or biomarkers in manners including, but not limited to, uptake, selective uptake, diffusion, and attachment to the linking molecule. The linking molecule may be an antibody to bind to an antigen, a biomarker, a chemoattractant molecule, an organic molecule (e.g. a protein, a lipid, a sugar), a drug, combinations thereof, or the like. The linking molecule can allow for conjugation of the detection moiety to the target analyte, or even the non-target analyte, where appropriate. The bond, and related attraction, may be covalent or non-covalent, including bonding such as ionic, dipole-dipole interactions, London dispersion forces, van der Waal's forces, hydrophobic interactions, and hydrogen bonding. For instance, a detection moiety may be attached to an EpCAM antibody, thereby forming an EpCAM antibody-detection moiety complex. When the EpCAM antibody-detection moiety complex is introduced to a target material with an EpCAM biomarker, the EpCAM biomarker and the EpCAM antibody can attract and bond to each other, thereby attaching the detection moiety to the target material. In another example, a detection moiety may be attached to an avidin, such as streptavidin or neutravidin, thereby forming an avidin-detection moiety complex. When the avidin-detection moiety complex is introduced to a target material with a biotin molecule on the outer surface, the biotin and avidin attract and bond to each other, thereby attaching the detection moiety to the target material. A set of stains, which includes at least two stains and may include up to 4, 6, 8, 10, or more, may be used to label the target material in parallel or in series (i.e. multiplex), such that each stain binds to a different antigen on or within the target material.

The sample may then be imaged after labeling the at least one target analyte. To image, the substrate, including the sample with at least one target analyte, is introduced into the scanner 100, such as a fluorescent microscope. An analysis area of the sample is illuminated with one or more wavelengths of light, such as red, blue, green, and violet or ultraviolet, from the at least one light source 126 or a plurality of light sources. The light from the light source to illuminate the analysis area may be referred to as "excitation light." The excitation light is emitted by the light source and focused by and passed through an objective to the analysis area on the substrate. The light source and the objective may be separate pieces or may be one piece. The different wavelengths excite different detection moieties based on the absorption spectra of the respective detection moieties, thereby causing the detection moiety to emit light at a particular wavelength. The light emitted by the excited detection moiety, also known as the "emission light," bound to the target analyte can be captured by the objective 110 and transmitted to an image detector 130. The image detector 130, such as a charge-coupled device ("CCD") or scientific CMOS camera, captures the image data. A mirror 128, such as a polychroic or dichroic mirror, may be used to reflect the excitation light from the light source 124 and permit passage of the emission light to the image detector 130. Once all of the desired excitation lights have been used to illuminate the analysis area, a new analysis area is illuminated. The process continues until the entire sample has been illuminated by the respective excitation lights and the appropriate data has been collected.

For example, when using a 4-wavelength scan, a slide with a sample labeled with four stains is inserted into the scanner. A first analysis area is brought within a field of view and a proper focal plane and subsequently illuminated by four excitation lights, such that no two excitation lights have the same wavelength. Each excitation light excites one of the four stains on the sample. The emission light from each stain is captured the objective and transmitted to the image detector 130. The slide or the imaging system (such as the light source, objective, and image detector) may move to bring a second analysis area within the field of view and the proper focal plane. The second analysis area is then illuminated by the four excitation wavelengths. The emission lights are captured and transmitted. The process repeats until data for the entire sample has been obtained.

It should be further noted that though four wavelengths and detection moieties were described, this process may be used for any number of wavelengths and detection moieties, such as up to 2, 3, 5, 6, 8, 10, 20, 50, or 100, where appropriate. Furthermore, though four excitation lights are discussed, fewer or more excitation lights may be used. For example, one excitation light may excite at least two different detection moieties, such that each detection moiety has a different emission wavelength. Therefore, regardless of the number of excitation lights and detection moieties used, the number of excitation-emission pairings may equal the desired number of targets to be labeled. Alternatively, two excitation lights may excite one detection moiety to increase the signal provided by the detection moiety.

Imaging may be done in brightfield and/or darkfield illumination, phase contrast, differential interference contrast, fluorescence, and Hoffman modulation contrast. The images formed from the emission light of each detection moiety can be overlaid when a plurality of detection moieties are excited and emit light. Though emission is discussed above, reflection, diffraction, scatter, and combinations thereof may be used in addition or alternatively to emission detection/imaging.

After imaging, the scanner 100 may transmit the data back to an external device 132 or may be retained within the scanner 100. The external device 132 or scanner 100 may then implement a non-transitory computer-readable medium process to evaluate and process the data. The non-transitory computer-readable medium process may detect a candidate object, such as the at least one target analyte. Candidate objects, such target analytes, may be found using at least one image processing technique, including, but not limited to, thresholding (manual or automatic), template matching, watershedding, cross-correlation, convolutional neural networks, region growing, and edge detection. For example, after imaging, the data may then be compiled into images, processed, and analyzed by a computer or associated software or programs, whereby the at least one target analyte may be characterized. The images may be analyzed to detect, enumerate, and locate the at least one target analyte. The images formed due to the emission lights may be overlaid when a plurality of detection moieties, having bound themselves to the target analyte, are excited and emit light. Imaging may be performed in a tube, on a microscope slide, or in any appropriate vessel or substrate for imaging.

The non-transitory computer-readable medium process may also determine the location(s) of the target analyte(s) on the substrate. During the detection step, the location(s) of the target analyte(s) are recorded using a coordinate system. For example, when the substrate 122 is a slide, a short side of the substrate 122 is a first axis of coordinate system, such as the x-axis or y-axis, and a long side of the substrate 122 is a second axis of the coordinate system, such as the y-axis or the x-axis. In one embodiment, when the first side 123 of the substrate 122 including the target analyte 140 is imaged facing the image detector 130, the first objective 110, and the at least one light source 124 and facing away from the picker 102 (i.e. the detector 130, the first objective 110, and the at least one light source 124 are on a side of the substrate opposite the picker 102), geometrical or coordinate-based adjustments may be made to the coordinates such that the coordinates are adjusted to account for a change in substrate orientation when the first side then faces the picker 102 for at least the isolating step. For example, the at least one target analyte 140 may be located at (−1, 2) during imaging. To pick, the substrate 122 may be flipped over. For example, a microscope slide, being rectangular, may be rotated 180 degrees along a long or short axis. To account for the change in location due to the flipping, geometrical adjustments are made to now account for the at least one target analyte 140 being located at different location relative to the picker 102, the at least one light source 124, and the image detector 130. Though the location of the target analyte 140 relative to the substrate 122 on which the target analyte 140 resides is the same, the location relative to the components of the scanner 100 changes due to the rotating or flipping step. The new location may then be used for the following steps, including isolation. In one embodiment, the first side 123 of the substrate 122 including the target analyte 140 is imaged facing the picker 102, such that no geometrical or coordinate-based adjustments to the at least one target analyte 140 location are needed for subsequent steps (i.e. in one embodiment the image detector 130, the first objective 110, and the at least one light source 124 are on the same side of the substrate 122 as the picker 102; or, in one embodiment). For example, the at least one target analyte 140 may be located at (−1, 2) during imaging. Since no changes in location occur, the at least one target analyte 140 is located at (−1, 2). This location may then be used for the following steps, including isolation.

An operator or a non-transitory computer-readable medium may then select the at least one target analyte to be isolated from the sample, such as by picking. To pick the at least one target analyte, the surface of the substrate 122 may first be located. One of the manners by which to detect the surface of the substrate, as discussed above, may be employed. In one embodiment, the surface of the substrate 122 at the location of the at least one target analyte may be detected, whereby the opening of the picker tip 104 partially or fully envelops the at least one target analyte. In one embodiment, the surface of the substrate 122 is not detected directly at the location of the at least one target analyte. The surface of the substrate 122 is detected up to 1000 μm, including up to 1 nm, 2 nm, 3 nm, 5 nm, 10 nm, 15 nm, 20 nm, 25 nm, 50 nm, 75 nm, 100 nm, 125 nm, 200 nm, 250 nm, 500 nm, 750 nm, 1 μm, 2 μm, 3 μm, 5 μm, 10 μm, 15 μm, 20 μm, 25 μm, 50 μm, 75 μm, 100 μm, 125 μm, 200 μm, 250 μm, 500 μm, and 750 μm, from the location of the at least one target analyte.

In one embodiment, after detecting the surface of the substrate 122, the picker 102 including the picker tip 104 is withdrawn from the surface of the substrate 122. The picker 102 including the picker tip 104 may be withdrawn to a holding position. The holding position may be a pre-determined distance from the surface of the substrate 122 (i.e. withdraw up to 1 millimeter from the substrate surface) or may be a set distance withdrawn to from the surface of the substrate 122 (i.e. withdraw to a distance of up to 1 millimeter from the substrate surface). The picker tip 104 may then be re-positioned to partially or fully envelop the target analyte or to be located above the target analyte along the z-axis. In one embodiment, after detecting the surface of the substrate 122, the picker tip 104 is not withdrawn and the at least one target analyte is isolated from the substrate 122.

To isolate the at least one target analyte from the substrate 122, at least one of the following actions may be performed. In one embodiment, a pressure gradient may be introduced by the picker 102 thereby causing the at least one target analyte to move into the picker tip 104. In another embodiment, the picker tip 104 may then be moved horizontally or orthogonally to detach the least one target analyte from the substrate 122. The pressure gradient may then be introduced to draw the least one target analyte into the picker tip 104. In one embodiment, the picker tip 104, after being placed above or over the least one target analyte, may oscillate up and down at any appropriate frequency to detach the least one target analyte from the substrate 122, such as, for example, less than or equal to approximately 10 kHz. The pressure gradient may then be introduced to draw the least one target analyte into the picker tip 104. In one embodiment, the picker tip 104 may be placed above or over the least one target analyte and the least one target analyte may be held within the picker tip 104 without actively applying the pressure gradient. In one embodiment, the picker tip 104 may be placed above or over the least one target analyte and dragged across the surface of the substrate 122, thereby dislodging the least one target analyte and causing the least one target analyte to be held within the picker tip 104 without actively applying the pressure gradient. In one embodiment, a permanent magnet or electromagnet may be engaged and/or activated so as to remove at least one target analyte bound to a magnetic particle.

The at least one target analyte, once isolated, may be dispensed onto or into a secondary vessel and analyzed using any appropriate analysis method or technique, though more specifically intracellular analysis including intracellular or extracellular protein labeling; nucleic acid analysis, including, but not limited to, protein or nucleic acid microarrays; FISH; bDNA analysis; next-gen sequencing; PCR. These techniques require isolation, permeabilization, and fixation of the target analyte prior to analysis. Some of the intracellular proteins which may be labeled include, but are not limited to, cytokeratin ("CK"), actin, Arp2/3, coronin, dystrophin, FtsZ, myosin, spectrin, tubulin, collagen, cathepsin D, ALDH, PBGD, Akt1, Akt2, c-myc, caspases, survivin, $p27^{kip}$, FOXC2, BRAF, Phospho-Akt1 and 2, Phospho-Erk1/2, Erk1/2, P38 MAPK, Vimentin, ER, PgR, PI3K, pFAK, KRAS, ALKH1, Twist1, Snail1, ZEB1, Slug, Ki-67, M30, MAGEA3, phosphorylated receptor kinases, modified histones, chromatin-associated proteins, and MAGE. In order to fix, permeabilize, or label, fixing agents (such as formaldehyde, formalin, methanol, acetone, paraformaldehyde, or glutaraldehyde), detergents (such as saponin, polyoxyethylene, digitonin, octyl β-glucoside, octyl β-thioglucoside, 1-S-octyl-β-D-thioglucopyranoside, polysorbate-20, CHAPS, CHAPSO, (1,1,3,3-Tetramethylbutyl)phenyl-polyethylene glycol or octylphenol ethylene oxide), or labeling agents (such as fluorescently-labeled antibodies, Pap stain, Giemsa stain, or hematoxylin and eosin stain) may be used.

The steps, or a portion of the steps, of surface detection through analyzing may be repeated as many times as desired for as many target analytes as desired. In other words, the driving, contacting, overtraveling, and isolating steps are repeated n more times for the n more target analytes, where n is greater than or equal to 1. For example, the driving, contacting, overtraveling, and isolating steps are repeated 1 more time for 1 more target analyte; the driving, contacting, overtraveling, and isolating steps are repeated 2 more times for 2 more target analytes; and so on. It should be noted that these steps are performed for each desired target analyte to account for deformations, inconsistencies, or variations across the surface of the substrate. The deformations, inconsistencies, or variations may include, but are not limited to, height differences, angular differences, cracks, chips, bumps, or the like.

During the substrate detection steps, the z-picker motor system, the sensor 202, and the target plate 204 may form an open loop, as the location of the picker tip 104 relative to the surface of the substrate is unknown. After detecting the surface of the substrate at a first location and withdrawing the picker tip 104, the z-picker motor system, the sensor 202, and the target plate 204 may then form a closed feedback loop, as the location of the location of the picker tip 104 relative to the surface of the substrate is known and may be positioned or moved accordingly. The z-picker motor system, the sensor 202, and the target plate 204 may then revert to open loop when detecting the surface of the substrate at a second location. After detecting the surface of the substrate at the second location and withdrawing the picker tip 104, the z-picker motor system, the sensor 202, and the target plate 204 may then form the closed feedback loop. This process may be repeated as many times as necessary based on the number of target analytes to be isolated.

In one embodiment, at least one non-transitory computer-readable medium including computer-executable instructions, which when executed on one or more computers, perform the method (or a portion thereof) discussed above, is considered. A computer-readable medium includes, but is not limited to, magnetic and optical storage devices such as disk drives, magnetic tape, CDs (compact disks), DVDs (digital versatile discs or digital video discs), and semiconductor devices such as RAM, DRAM, ROM, EPROM, and Flash memory. The instructions may be executed as firmware and/or software. The instructions may be stored in the scanner 100, on the external device 132, or on an external server or storage device. The instructions may be a single program or may be divided across a plurality of programs, wherein each program contains a subset of the instructions. The instructions may also be stored in full in several instruments (i.e. the scanner 100 and the external device 132 may each have the full set of instructions).

In one embodiment, a processor 124 may be implemented as a microcontroller including memory for the storage of data and firmware and/or software for execution. In one embodiment, the processor 124 may be implemented as a microcontroller with separate memory. In one embodiment, the processor 124 may control both the scanner 100 and the external device 132. In one embodiment, the processor 124 may control the scanner 100 and a separate processor may control the external device 132. In one embodiment, the scanner 100 or the external device 132 may include a single processor and the other one of the scanner 100 or the computer (not shown) external to the scanner 100 may include a plurality of processors, wherein each of the plurality of processors is configured to operate, control, or perform different functions. In one embodiment, the scanner 100 and the external device 132 may each include a plurality of processors, wherein each of the plurality of processors is configured to operate, control, or perform different functions. It should be noted that when the external device 132 is not included or implemented, the scanner 100 may include an input device, such as a keyboard or a touch screen, to input data, instructions, or the like.

The foregoing description, for purposes of explanation, used specific nomenclature to provide a thorough understanding of the disclosure. However, it will be apparent to one skilled in the art that the specific details are not required in order to practice the systems and methods described herein. The foregoing descriptions of specific embodiments are presented by way of examples for purposes of illustration and description. They are not intended to be exhaustive of or to limit this disclosure to the precise forms described. Many modifications and variations are possible in view of the above teachings. The embodiments are shown and described in order to best explain the principles of this disclosure and practical applications, to thereby enable others skilled in the art to best utilize this disclosure and various embodiments with various modifications as are suited to the particular use contemplated. It is intended that the scope of this disclosure be defined by the following claims and their equivalents:

We claim:

1. A system comprising:
a picker comprising a picker tip;
a substrate comprising
a first side comprising a first target analyte, and
a second side;
a substrate holder comprising the substrate,
a position detector comprising
a sensor fixed at a set distance along a first axis relative to the substrate holder,
a target plate fixed at a set distance along the first axis relative to the picker tip; and
at least one processor programmed to execute a method comprising
driving the picker along the first axis towards the first side of the substrate,
wherein, during the driving step, the sensor or the target plate moves toward or away from the target plate or the sensor, respectively,
contacting the substrate with the picker tip,
overtraveling the substrate with the picker tip,
withdrawing the picker tip from the substrate to at least the point along the first axis at which the contacting step occurs, wherein the withdrawing step is performed after the overtraveling step and before the isolating step, and
isolating the first target analyte from the substrate with the picker.

2. The system of claim 1, further comprising at least one motor controlled by the processor to execute at least one of the driving, contacting, or overtraveling steps.

3. The system of claim 1, further comprising
at least one light source; and
a detector.

4. The system of claim 3, wherein the picker is located on the first side of the substrate; and wherein the detector and the at least one light source are located on the second side of the substrate opposite the picker.

5. The system of claim 4, wherein the first target analyte is labeled with at least one stain.

6. The system of claim 5, wherein the method further comprises:
  initiating the at least one light source to emit light comprising at least one wavelength;
  detecting the at least one stain with the detector based on a signal provided or caused by the at least one stain; and
  determining a location of the first target analyte on the substrate.

7. The system of claim 6, wherein the initiating, detecting, and determining steps occur before the driving, contacting, overtraveling, and isolating steps.

8. The system of claim 7, wherein the method further comprises moving the substrate along at least one axis perpendicular to the first axis to orient the first target analyte underneath an opening of the picker tip such that the opening, when the picker undergoes the driving and contacting steps, partially or fully envelops the first target analyte.

9. The system of claim 8, wherein the moving step occurs after the initiating, detecting, and determining steps and before the driving, contacting, overtraveling, and isolating steps.

10. The system of claim 7, wherein the initiating and detecting steps are performed with the first side facing the detector and the at least one light source; and wherein the driving, contacting, overtraveling, and isolating steps are performed with the first side facing the picker.

11. The system of claim 6, further comprising a plurality of processors, wherein each processor is programmed to execute a subset of the method.

12. The system of claim 11, wherein a first processor is located within a scanner, and wherein a second processor is located within an external device in communication with the scanner.

13. The system of claim 1, wherein the at least one processor is located within a scanner or an external device in communication with the scanner.

14. The system of claim 1, wherein the substrate is a glass microscope slide.

15. The system of claim 14, wherein the picker tip is composed of a ceramic, glass, a metal, an organic material, an inorganic material, a plastic material, a polymer, a jewel, or combinations thereof.

16. The system of claim 14, wherein the picker tip exerts 0.01-16 ounces of force on the substrate during the overtraveling step.

* * * * *